(12) United States Patent
Jackson et al.

(10) Patent No.: US 10,206,716 B2
(45) Date of Patent: *Feb. 19, 2019

(54) BONE ANCHOR CLOSURE FLANGE FORM GUIDE AND ADVANCEMENT STRUCTURE WITH CONTROLLED SPLAY

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/852,866

(22) Filed: Dec. 22, 2017

(65) Prior Publication Data

US 2018/0132901 A1    May 17, 2018

Related U.S. Application Data

(63) Continuation of application No. 15/665,116, filed on Jul. 31, 2017, now Pat. No. 9,861,394, which is a continuation of application No. 14/581,165, filed on Dec. 23, 2014, now Pat. No. 9,717,533, which is a continuation-in-part of application No. 14/569,142, filed on Dec. 12, 2014.

(60) Provisional application No. 61/920,033, filed on Dec. 23, 2013, provisional application No. 61/915,085, filed on Dec. 12, 2013.

(51) Int. Cl.
  *A61B 17/70* (2006.01)

(52) U.S. Cl.
  CPC ............... *A61B 17/7032* (2013.01)

(58) Field of Classification Search
  CPC .................................................. A61B 17/686
  See application file for complete search history.

(56) References Cited

U.S. PATENT DOCUMENTS

| | | |
|---|---|---|
| 2,005,348 A | 6/1935 | Michell |
| 2,833,325 A | 5/1958 | Laisy |
| 4,600,225 A | 7/1986 | Blose |
| 5,067,955 A | 11/1991 | Cotrel |
| 5,092,635 A | 3/1992 | DeLange et al. |
| 5,234,430 A | 8/1993 | Huebner |
| 5,334,203 A | 8/1994 | Wagner |
| 5,605,458 A | 2/1997 | Bailey et al. |
| 5,607,304 A | 3/1997 | Bailey et al. |
| 5,672,176 A | 9/1997 | Biedermann et al. |
| 5,797,911 A | 8/1998 | Sherman et al. |
| 6,006,930 A | 12/1999 | Dreyer et al. |
| 6,010,502 A | 1/2000 | Bagby |

(Continued)

FOREIGN PATENT DOCUMENTS

| | | |
|---|---|---|
| DE | 20207850 U1 | 10/2002 |
| WO | WO 95/13755 | 5/1995 |

OTHER PUBLICATIONS

European Search Report, EP14189707.4, dated Feb. 25, 2015.

*Primary Examiner* — Jan Christopher Merene
(74) *Attorney, Agent, or Firm* — Polsinelli PC

(57) ABSTRACT

Open implant closure structures include a helically wound guide and advancement flange form having pivot-splay accommodating and splay control surfaces with opposing load flanks in initial non-parallel relation.

10 Claims, 9 Drawing Sheets

(56) References Cited

U.S. PATENT DOCUMENTS

| | | |
|---|---|---|
| 6,063,090 A | 5/2000 | Schlapfer |
| 6,077,262 A | 6/2000 | Schlapfer et al. |
| 6,077,267 A | 6/2000 | Huene |
| 6,254,146 B1 | 7/2001 | Church |
| 6,296,642 B1 | 10/2001 | Morrison et al. |
| 6,412,831 B1 | 7/2002 | Noel et al. |
| 6,554,834 B1 | 4/2003 | Crozet et al. |
| 6,730,089 B2 | 5/2004 | Jackson |
| 6,997,927 B2 | 2/2006 | Jackson |
| 7,204,838 B2 | 4/2007 | Jackson |
| 7,250,052 B2 | 7/2007 | Landry et al. |
| 7,717,942 B2 | 5/2010 | Schumacher |
| 7,766,945 B2 | 8/2010 | Nilsson et al. |
| 7,794,477 B2 | 9/2010 | Melkent et al. |
| 7,972,364 B2 | 7/2011 | Biedermann et al. |
| 8,162,989 B2 | 4/2012 | Khalili |
| 8,382,809 B2 | 2/2013 | Kaufman et al. |
| 8,814,913 B2 | 8/2014 | Jackson |
| 8,828,060 B2 | 9/2014 | Biedermann et al. |
| 8,911,479 B2 | 12/2014 | Jackson et al. |
| 9,068,587 B2 | 6/2015 | Sage et al. |
| 9,445,847 B2 | 9/2016 | Biedermann et al. |
| 9,636,146 B2 | 5/2017 | Jackson et al. |
| 9,717,533 B2 | 8/2017 | Jackson et al. |
| 9,743,957 B2 | 8/2017 | Jackson |
| 9,861,394 B2 * | 1/2018 | Jackson ............ A61B 17/7032 |
| 10,004,541 B1 | 6/2018 | Jackson |
| 2002/0143341 A1 | 10/2002 | Biedermann et al. |
| 2003/0023243 A1 | 1/2003 | Biedermann et al. |
| 2003/0100904 A1 | 5/2003 | Biedermann |
| 2003/0149431 A1 | 8/2003 | Varieur et al. |
| 2004/0049196 A1 | 3/2004 | Jackson |
| 2004/0138662 A1 | 7/2004 | Landry et al. |
| 2004/0143265 A1 | 7/2004 | Landry |
| 2004/0147929 A1 | 7/2004 | Biedermann et al. |
| 2004/0167524 A1 | 8/2004 | Jackson |
| 2004/0167525 A1 | 8/2004 | Jackson |
| 2004/0172032 A1 | 9/2004 | Jackson |
| 2004/0186474 A1 | 9/2004 | Matthis et al. |
| 2005/0182410 A1 | 8/2005 | Jackson |
| 2005/0216003 A1 | 9/2005 | Biedermann et al. |
| 2005/0277928 A1 | 12/2005 | Boschert |
| 2006/0009773 A1 | 1/2006 | Jackson |
| 2006/0083603 A1 | 4/2006 | Jackson |
| 2007/0208344 A1 | 9/2007 | Young |
| 2008/0215100 A1 | 9/2008 | Matthis et al. |
| 2008/0269809 A1 | 10/2008 | Garamszegi |
| 2008/0292429 A1 | 11/2008 | Hasenbohler et al. |
| 2013/0013003 A1 | 1/2013 | Carbone et al. |
| 2014/0081334 A1 | 3/2014 | Jackson |
| 2014/0142633 A1 | 5/2014 | Jackson et al. |
| 2014/0214097 A1 | 7/2014 | Jackson et al. |
| 2015/0119942 A1 | 4/2015 | Jackson et al. |
| 2015/0131421 A1 | 5/2015 | Mimura |
| 2015/0148846 A1 | 5/2015 | Jackson |
| 2015/0164558 A1 | 6/2015 | Jackson et al. |
| 2016/0038188 A1 | 2/2016 | Jackson et al. |
| 2016/0242818 A1 | 8/2016 | Jackson |
| 2017/0189073 A1 | 7/2017 | Jackson et al. |
| 2017/0333083 A1 | 11/2017 | Jackson et al. |
| 2017/0354441 A1 | 12/2017 | Jackson et al. |
| 2017/0354443 A1 | 12/2017 | Jackson |

\* cited by examiner

BONE ANCHOR CLOSURE FLANGE FORM GUIDE AND ADVANCEMENT STRUCTURE WITH CONTROLLED SPLAY

CROSS-REFERENCE TO RELATED APPLICATIONS

This application is a continuation of U.S. application Ser. No. 15/665,116, filed Jul. 21, 2017, which is a continuation of U.S. application Ser. No. 14/581,165, filed Dec. 23, 2014, which claims the benefit of U.S. Provisional Patent Application No. 61/920,033, filed Dec. 23, 2013. U.S. application Ser. No. 14/581,165 is also a continuation in part of U.S. application Ser. No. 14/569,142, filed Dec. 12, 2014, which claims the benefit of U.S. Provisional Patent Application No. 61/915,085, filed Dec. 12, 2013. Each of these applications is incorporated by reference herein in its entirety for all purposes.

BACKGROUND OF THE INVENTION

The present invention is directed to structure for joining together parts of a medical implant, in particular for use with open bone anchors in spinal surgery, and in some embodiments thereof, for use with spinal bone anchors such as polyaxial screws having upwardly extending arms with helically wound guide and advancement structures.

Bone anchors, such as bone screws and hooks, are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a longitudinal connecting member, such as a rod connector, or are supported by the connector. Although both closed-ended and open-ended bone anchors are known, open-ended anchors are particularly well suited for connections to longitudinal connecting members such as hard, soft or deformable rods, dynamic, soft or elastic connectors and connector sleeves or arms, because such rods or other connector members do not need to be passed through a closed bore, but rather can be laid or urged into an open channel within a U-shaped receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit that includes the open channel for receiving a rod connector or other longitudinal connecting member.

Typical open-ended bone screws include a threaded shank with a head or receiver having a pair of parallel projecting branches or arms which form a yoke with a U-shaped slot or channel to receive a portion of a rod or other longitudinal connecting member. Hooks and other types of connectors, as are used in spinal fixation techniques, may also include similar open ends for receiving rods or portions of other fixation and stabilization structure. After the rod or other longitudinal connecting member is placed in the receiver channel, a closure, typically in the form of a substantially cylindrical plug is often used to close the channel. Known closures include slide-on types, twist-on varieties that are rotated ninety degrees to a locked in position, and a variety of single start helically wound guide and advancement structures including, for example, thread forms having v-thread, reverse-angle, buttress or square thread forms, to name a few, as well as other non-threadlike helically wound forms, such as helical flanges.

It is known that the angled loading flank of a v-thread closure generates outward splay of spaced open implant receiver arms at all loading levels without limit. Thus, v-threaded closures or plugs are sometimes used in combination with outer threaded nuts that prevent outward splaying of the receiver arms. To overcome the splay problems of v-threaded closures, so-called "buttress" thread forms were developed. In a buttress thread, the trailing or thrust surface is linear and oriented somewhat downwardly in the direction of advancement with respect to the thread axis, while the leading or clearance surface is angled rearwardly in varying degrees, theoretically resulting in a neutral radial reaction of a threaded receptacle or receiver to torque on the threaded closure member being received thereby. In reverse angled thread forms, which theoretically positively draw the threads of a receptacle radially inwardly toward the thread axis when the reverse angle closure thread is torqued, provided the outer tip of the thread is crested and strong enough, the trailing linear surface of the external thread of the closure is angled somewhat upwardly toward the thread axis instead of away or somewhat downwardly from the thread axis (as in conventional v-threads). Although buttress and reverse angle threads with linear loading surfaces reduce the tendency of bone screw receiver arms to splay outwardly, they are not structured to control it and the arms may still be flexed outwardly by bending moment forces acting on the implant arms and the closure threads can be bent, deformed or even sheared off by forces exerted during installation, as well as experienced post-operatively on the implants with certain activities.

Closures made with square threads, again, having linear loading surfaces, theoretically keep all forces axially directed. However, it has been found that under a moderate load, square thread closures produce a marginal splay and under heavy load, splay can be considerable, indicating that traditional square thread machine design theories directed to power screws and other screws for use in substantially closed bores do not adequately describe and reflect the environment of a spinal open bone screw receiver having a relatively small size with spaced apart arms in lieu of a bore. Furthermore, square threaded spinal bone anchor closures have been shown to experience heretofore unexplained and undesirable excess stress concentrated on their upper outer loading flank portions located near the crest of the thread believed by Applicants to be due to outwardly directed rotational pivot and displacement of the mating receiver arm thread flank portions when under the stress of loading between the arms of an open receiver. This occurs during intra-operative tightening and post-operative physiologic loading, which is believed to have resulted in in-vivo loosening in some cases.

SUMMARY OF THE INVENTION

A spinal implant closure structure embodiment according to the invention that includes a closure structure or plug mated with opposed arms of an open bone anchor includes splay allowance and splay arresting surfaces for holding a spinal fixation longitudinal connecting member, such as a rod, the anchor having an open receiver with spaced apart arms defining a longitudinal connecting member receiving channel therebetween. Embodiments of the present invention provide distinct dissimilar mating guide and advancement flange forms on the closure and cooperating receiver arms to allow, but ultimately control pivot splay of the arms when the closure is rotated and advanced between the arms and thereafter tightened, and wherein adequate and desired locking thrust is generated in so doing. Specifically, embodiments of the invention initially allow for some splay that has been found to reduce torque and improve thrust during initial loading of the closure into the receiver arms and then aid in splay control during torquing or tightening of the closure with respect to the arms that occurs when the closure abuts against an insert located in the receiver or directly against a longitudinal connecting member.

According to an aspect of the invention, the closure flange form includes a first portion located adjacent a root of the form and extending radially outwardly therefrom in a direction away from the central axis, the first portion having a first load flank surface that terminates at a first splay control ramp having another surface sloping upwardly and outwardly at some predetermined angle. A discontinuous receiver flange form second load flank surface is configured to form an acute angle with the closure first load flank surface and engage the closure first load flank at a vertex of such acute angle, the vertex being located substantially medial of the closure splay control ramp. Stated in another way, the closure flange form first load surface and cooperating bone anchor receiver flange form second load surface are configured to be oriented at least initially toward one another in a nonparallel contact relationship early in the loading and tightening process with such contact initially located near the closure root surface. When the closure is tightened against a rod or other bone anchor feature later in an assembly process, the location of contact between the closure load surface and the receiver load surface may migrate slightly toward the closure flange form crest, but remains close to the closure root with the acute angle between the load surfaces reducing slightly due to pivot splay occurring in the upright arms of the receiver. Radially outward portions of the load flanks remain spaced from one another even when the closure is tightly fixed to the bone anchor. The closure flange form also has a second portion extending radially outwardly from a termination of the load flank to a crest of the flange form. The second portion includes the first splay control ramp and a raised toe that can be contoured or rounded, and which has an upper surface that remains unloaded in use, the toe being spaced from the first load flank both radially and axially.

The discontinuous receiver guide and advancement flange form extends helically about and along an inner surface of each receiver arm, the receiver flange form having the second load flank and a second splay control ramp. The second load flank engaging the first load flank at an angle as set forth above and the second splay control ramp ultimately engaging the first splay control ramp to arrest outward receiver arm rotational splay, the receiver flange form having clearance surfaces disposed in close spaced relation to a remainder of the closure flange form. Thus, the receiver arm flange forms are not typically identical in shape and size to the closure flange form. For example, if the closure load flank is substantially horizontal, the cooperating receiver load flank is oriented at a slight reverse angle. If, however, the closure load flank slopes in a downward and outward direction from the closure root, then the receiver load flank may be oriented generally horizontally. Likewise, if the closure load flank slopes upwardly and outwardly from the closure root, the cooperating receiver load flank may be further undercut to provide an angle of inclination between the two loading surfaces to accommodate an acceptable amount of outward splaying of the receiver arms that also includes an outward pivot of the arms which is identified herein by the term "pivot-splay." Because the closure and receiver loading flanks are always at an acute angle to one another, contact between the loading flanks remains close to the closure root during pivot-splay of the receiver arms. At an acceptable level of receiver pivot-splay, the splay control ramps of the closure and receiver engage, arresting any further undesirable pivot-splay of the receiver arms and the loading flanks can be slightly more parallel with respect to each other.

Other aspects of the invention include sizing the closure flange form to capitalize on tensile forces by reducing flange form depth and variable sizing of the closure unloaded toe to strengthen the closure mechanism.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
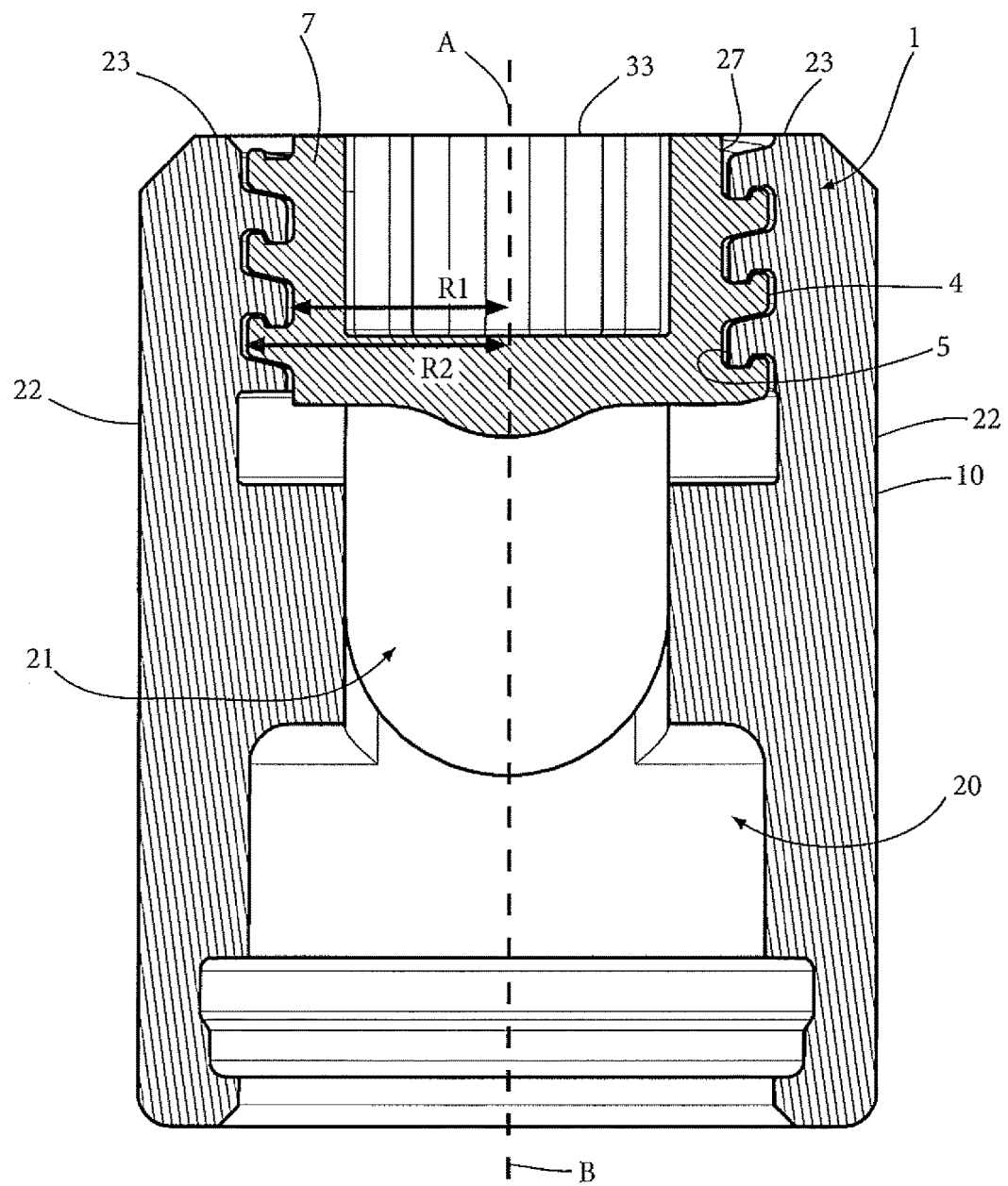
FIG. 1 is a front elevational view of a portion of a spinal implant showing only a rod receiver and a closure and with portions broken away to show the detail of a closure flange form mechanism according to an embodiment of the invention.

As required, detailed embodiments are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

It is noted that helically wound pivot-splay accommodating and controlling flange forms described in detail herein cannot be considered thread forms as flange forms include numerous features, including surfaces and contours, some which may be compound and non-linear, in addition to and not anticipated by traditional screw thread technology and nomenclature. However, certain terms used in this application will be similar to those used in thread form nomenclature. For example, in traditional v-thread nomenclature, a flank is often described as a thread face running from a root to a crest of a thread form with the root being the bottom surface joining flanks of two adjacent flanks and the crest being the top and bottom surfaces joining two flanks of a single thread form near an outer edge or tip thereof. In this application, the term flank may be used to describe certain surfaces of a flange form, such as a loading or thrust surface, but unlike a thread, a flange form flank does not necessarily connect a root to a crest of a particular form. Similarly, a crest or outermost edge surface of a flange form does not necessarily function as the surface that joins two flanks as other features, such as splay control surfaces and/or unloaded curves or contours, may be located between a flank and a crest. Furthermore, while a root surface of a flange form may typically be substantially cylindrical and a crest surface of a flange form may be at least partially cylindrical, such surface may also be sloped or curved. Thus, an entire outer surface which might be identified as a "crest" surface of a closure plug may or may not be at a uniform distance from a cooperating root surface.

Also, the terms lead, pitch and start, as such terms are used to describe other helically wound guide and advancement structures, are to be understood as follows: Lead is a distance along the axis of a closure or plug that is covered by one complete rotation (360 degrees) of the closure with respect to a mating structure. Pitch is the distance from a location on a crest or most outward surface of one flange form structure to the same location on the next or adjacent flange form. For example in a single-start thread-form, such as a single start, helically wound v-thread closure plug, lead and pitch are the same. Single start means that there is only one helically wound form wrapped around a cylindrical core, or in the case of embodiments of closures according to the present invention, wrapped around a cylindrical closure plug body and thus there is only one start structure or surface at a base or forward end of the closure body that initially engages a mating structure on an open implant. Each time a single start closure rotates one turn (360 degrees), the closure has advanced axially by a width of one helical flange form. Double-start means that there are two forms wrapped around a core body and thus there are two starting surfaces or structures on the closure plug. Therefore, each time a double-start body rotates one turn (360 degrees), such a body has advanced axially by a width of two helical flange forms. Multi-start means that there are at least two and may be up to three or more of such forms wrapped around a core body. Similar to threads, flange forms may also be coarse or fine. Course flange forms are those with a larger pitch (fewer forms per axial distance) and fine forms have a smaller pitch (more forms per axial distance).

With particular reference to FIGS. 1-5, the reference numeral 1 generally indicates a closure mechanism in accordance with an embodiment of the invention that includes a male helical flange form, generally 4, rotatingly mated with a female helical flange form, generally 5. The form 4 is located on a bone implant closure 7 and the form 5 is located on opposed arms of an open bone anchor receiver 10. The receiver 10 is further part of a polyaxial bone screw apparatus or assembly that includes a shank (not shown) with a body having a bone engaging and implantation thread and also an upwardly extending substantially or partially spherical upper portion or head some or most of which may or may not be integral to the shank body. The receiver 10 has a cavity or inner chamber, generally 20, for receiving such a shank head, the cavity 20 communicating with an upper rod receiving channel, generally 21, formed between opposed arms 22 having top surfaces 23. The discontinuous flange form 5 is located near the top surface 23 of each arm 22 and faces inwardly toward the channel 21, winding helically downwardly in a direction toward the cavity 20 and thus defining an upper portion of the channel 21.

The illustrated closure 7 is a single piece structure with the flange form 4 having a single start and having an axis of rotation A. The closure top 7 mates under rotation with the receiver 10 having a central axis B with the axis A being aligned with the axis B. Closures according to the invention may take a variety of forms, including single and multi-start options, one piece closures, two piece closures, closures with break-off heads, closures with cannulation bores, for example, and may be used with a wide variety of medical implants, including, but not limited to mono-axial screws and hooks, hinged or uni-planar screws and hooks and dual multi-piece polyaxial bone screws and hooks, as well as screws with sliding or pivoting inserts. A variety of polyaxial bone screws may also be used with splay control structures of the invention and the illustrated embodiment should not be considered limiting. For example, splay control structures of the invention may be used with bone screws having top loaded bone screw shanks with spherical heads and also with bottom-loaded multi-part screw shanks as well as bottom loaded push or "pop-on" screws, such as Applicant's U.S. patent application Ser. No. 12/924,802, filed Oct. 5, 2010, for example, that is incorporated by reference herein. The closure 7 ultimately frictionally engages and presses against a longitudinal connecting member, for example, a rod connector (not shown), so as to capture, and fix the longitudinal connecting member within the receiver 10 and thus fix the member relative to a vertebra (not shown). The rod is typically hard, stiff, non-elastic and cylindrical, having an outer cylindrical surface. However, a longitudinal connecting member for use with bone anchors having the closure mechanism 1 may take the form of an elastic or deformable rod or have a different cross-sectional geometry. The longitudinal connecting member may also be a part of a soft or dynamic system that may include hard or soft structure for attaching to a bone anchor and may further include a tensioned cord, elastic bumpers and spacers located between bone screws, for example. In polyaxial embodiments, such as those illustrated in U.S. patent application Ser. No. 12/924,802, previously incorporated by reference herein, the receiver 10 and the shank cooperate in such a manner that the receiver 10 and the shank can be secured at any of a plurality of angles, articulations or rotational alignments relative to one another and within a selected range of angles both from side to side and from front to rear, to enable flexible or articulated engagement of the receiver 10 with the shank until both are locked or fixed relative to each other near the end of an implantation procedure.

With particular reference to FIGS. 2-5, the illustrated single-start closure 7 outer splay accommodating and control structure or flange form 4 operably joins with mating flange form structure 5 disposed on the arms 22 of the receiver 10 to result in the interlocking guide and advancement structure or arrangement, generally 1. Although one particular flange form structure and relationship, generally 1, will be described herein with respect to the forms 4 and 5, it is noted that there are a variety of flange form geometries, including, for example, those described in Applicant's U.S. patent application Ser. No. 11/101,859 filed Apr. 8, 2005 (US Pub. No. 2005/0182410 published Aug. 18, 2005), which is incorporated by reference herein as helpful background.

Each form 4 includes several surfaces or contours that helically wrap about the axis A. The contours of the flange form 42 include a root surface 27 that is helical and disposed substantially parallel to the axis A. A virtual cylinder formed by the root surface 27 has a radius R1 (radial distance between the axis A and the surface 27). Adjacent the root surface 27 is a radiused surface, curve or corner surface 28 that in turn is adjacent to a load or loading surface or flank 29. The load flank 29 is on a trailing side relative to a direction of advancement of the structure 4 along the receiver axis B when the structure 4 rotatingly mates with the flange form 5 on the receiver arms 22. In the illustrated embodiment, the load flank 29 also slopes slightly downwardly in a direction running radially outwardly from the root surface 27 toward an outer or crest surface 31 as indicated by a line FI on FIG. 2. However, the load flank 29 does not extend all of the way to the crest surface 31 as will be described in greater detail below. In some embodiments of the invention, the load flank 29, or at least portions thereof, may slope more steeply with respect to the horizontal, may be substantially horizontal (i.e., perpendicular to the axis A) or may even slope in a slightly upward direction toward a top surface 33 of the closure structure 7, i.e., reverse angle in nature. As will be discussed in more detail below, whatever the angular of orientation of the load flank 29 of the closure 7, an angular orientation of a cooperating adjacent load flank of the receiver 10 (indicated by a line F2 on FIG. 2) will be configured such that the opposing closure and receiver load flanks are in a non-parallel relationship so as to accommodate for pivot and thread tilt that occurs with receiver 10 arm pivot-twist-splay during rotational mating of the closure 4 within the receiver 10, setting an initial contact between the closure and receiver loading flanks at a position substantially medially on the male closure flank; in other words at a position at or close to the radiused surface 28 that transitions between the root surface 27 and the loading flank 29 of the closure flange form 4 (see, e.g., FIG. 5). It is noted that the downwardly sloping load flank 29 may actually cause some initial outward splay of the arms 22 during rotation of the form 4 into the form 5 which may be desirable as such an outward splay of the receiver arms 22 reduces torque and thus improves thrust of the closure 7 as it is driven into the receiver 10.

In certain embodiments, as is shown in the present illustration, a substantial portion of the crest surface 31 is substantially parallel to the root surface 27. Thus, a virtual cylinder formed by the crest surface 31 has a radius R2 (radial distance between the axis A and the surface 31). However, in other embodiments, the outer or crest surface may include radiused surfaces at a top and bottom thereof and may further have other sloping portions that are not parallel to the root surface. Thus, although the radial measurements R1 and R2 are substantially uniform for the illustrated embodiment, it is noted that in other embodiments, R1 would refer to the smallest distance from the axis A to a root surface or point 27 and R2 would refer to the greatest distance between the axis A and a crest surface or point 31. Furthermore, a distance D identifies a depth of the flange form 4 from the crest 31 to the root 27. Stated in another way, D=R2−R1. The distance or depth D may be further broken down into D1 and D2 wherein D1 is a distance from the crest surface 31 to the load flank 29 and D2 is a length of the load flank 29 measured from the root surface 27 to a location where the load flank 29 terminates. The distance D1 can be equal to, less than or greater than D2. The distance or depth D2 may preferably range from between about forty to about sixty percent of the total distance D.

Adjacent the loading flank 29 and running upwardly (in a direction toward the top surface 33) as well as outwardly toward the crest surface 31, is a splay control ramp or surface portion, generally 35 that in the illustrated embodiment includes a lower substantially frusto-conical surface 36 and an upper convex radiused surface portion 37. It is noted that although the splay control ramp 35 is ultimately an "anti-splay" structure for interlocking with the flange form 5 on the receiver arms 22, prohibiting undesirable outward splay of the arms 22 when in full locking engagement with the closure structure 7, it has been found that some limited splay and pivoting of the receiver arms 22 typically occurs and is even desirable as the splay beneficially reduces torque and desirably improves thrust during early loading of the closure into the receiver, but the splay control ramp advantageously arrests or limits such pivot-splay to a desired, acceptable amount.

In the illustrated embodiment, the radiused surface 37 is adjacent to another radiused surface 40 that curves outwardly and then downwardly, converging into the crest surface 31. The splay control ramp surfaces 36 and 37 and the upper rounded or radiused surface 40 define a protrusion, bead or toe, generally 41, of the flange form 4 that is directed generally upwardly toward the top surface 23 and is located outwardly away from the loading flank 29 and opposite a downward or leading facing heel or stab flank 42 of the form 4. The surfaces defining the toe 41 are spaced from the load flank 5, and, unlike the load flank 29, the toe 41 is never loaded, but always spaced from the flange form 5 of the receiver 10. It is noted that the load flank 29 may also be referred to as a thrust surface while the stab flank 42 may also be referred to as a clearance surface. To complete the illustrated flange form 4 geometry, a curved surface 46 made up of one or more radiused surface portions joins the stab surface 42 to the root surface 27.

Figure 4:
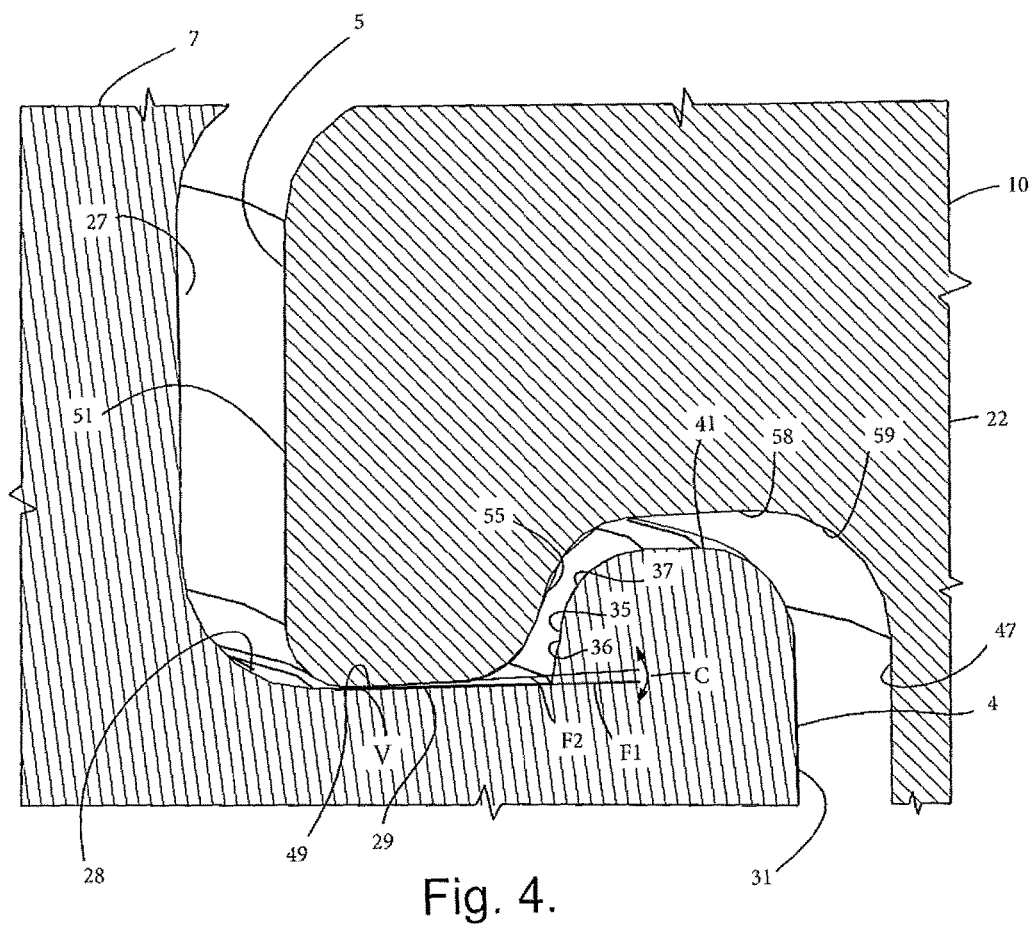
FIG. 4 is another enlarged and partial front elevational view with portions broken away of the closure flange form mechanism of FIG. 1 shown in an early mating and loading stage of assembly.
Figure 5:
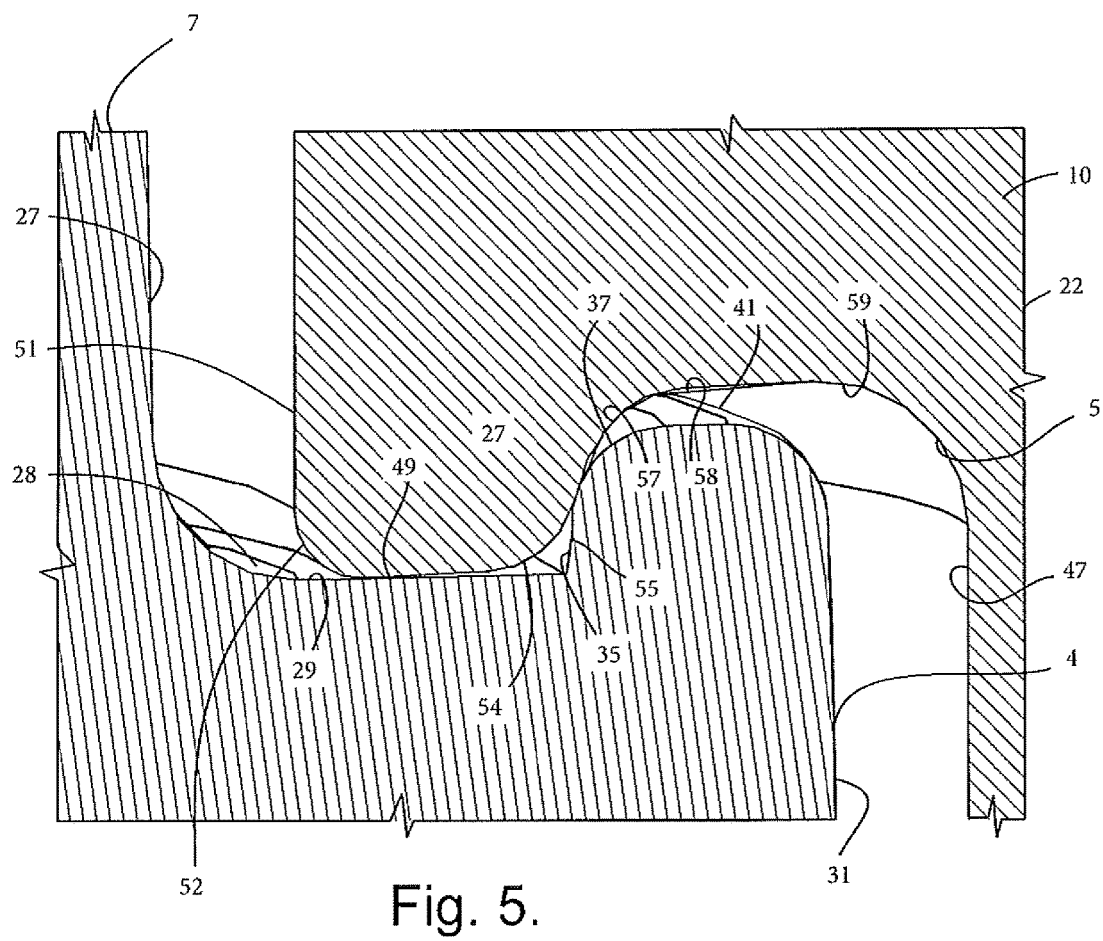
FIG. 5 is another partial front elevational view with portions broken away of the closure flange form mechanism of FIG. 4 shown in a subsequent tightening stage of assembly.

The discontinuous flange form 5 located on each receiver arm 22 cooperates with the form 4, but is not identical thereto or even a mirror image thereof. Rather, a balance is created between the flange form 4 and the flange form 5 to provide load and clearance surfaces to result in a desired splay control of the receiver arms 22. Also, cooperating loading flanks of the forms 4 and 5 are configured to allow for a desired amount of receiver pivot-splay during loading of the closure 4 into the receiver 10 and cooperating splay control ramps are configured to ultimately limit receiver pivot-splay during tightening of the closure 4 within the receiver 10. The flange form 5 includes a root surface 47, a load flank 49 and a crest surface 51. A radiused corner surface 52 connects the flank 49 and the crest surface 51. At an opposite side of the load flank 49 a radiused surface 54 joins the flank 49 with a splay control ramp 55. The splay control ramp 55 terminates at a location 57 that is adjacent a clearance surface 58 that extends toward the root surface 47. Another radiused surface 59 connects the clearance surface 88 with the root surface 47. At an opposite side of the root surface 47, another radiused corner surface 60 connects the root surface 47 with a stab flank or surface 64. To complete the geometry of the flange form 5, a radiused corner surface 65 connects the stab flank 64 with the crest surface 51. The flange form 5 load flank 49 frictionally engages the closure form 4 load flank 29. Unlike the closure form 4 toe 41 that does not engage the form 5 and thus is never loaded, the load flank 49 of the receiver flange form 5 may be identified as a loaded toe. Thus, although the flange form 4 looks very much like the flange form 5, similar geometric forms do not perform similarly. As is also shown in FIGS. 4 and 5, the splay control ramp 55 of the flange form 5 engages the splay control ramp 35 of the flange form 4 when the closure structure 7 is mated and torqued into tight locking engagement with the form 5 on the receiver arms 22.

In general, the load flanks 29 and 49 are positively engaged and axially loaded, that is, loaded in the direction of the axis A and axis B, when the closure 7 is advanced into the receiver arms 22. As relative torque between the closure 7 and the arms 22 increases by engagement with an insert or by engagement with a clamped member such as a rod connector, there is a tendency for the arms 22, to not only splay outwardly away from the axis A, but to also rotate and pivot outwardly. For example, see FIG. 3 that illustrates an outward pivot of the receiver arms 22 indicated by the arrow P. It is believed that a center of rotation X of the splay is located within each receiver upright arm 22 and would create unfavorable loading conditions for the closure flange form 4, placing additional stress as well as outward displacement on the closure load flank 29 if the receiver load flank 49 is configured to mate in a substantially parallel and flush manner with the flank 29. However, as illustrated by the extended lines F1 (runs along the load flank 29) and F2 (runs along the load flank 49) in FIG. 2, for example, the illustrated closure load flank 29 is disposed at an acute angle with respect to the load flank 49 of the receiver flange form 5. With particular reference to FIG. 4, during rotational mating of the closure 7 within the receiver 10 but prior to further loading or tightening, the receiver load flank 49 initially engages the closure load flank 29 in an non-parallel relationship, making contact at a location at or near the closure radiused surface 28 that is adjacent the closure root surface 27. Stated in another way, the discontinuous receiver thread form load flank surface 49 (see the extended line F2) is configured to form an acute angle with the closure load flank surface 29 (see the extended line F1) and engage the closure load flank 34 at a vertex V of an acute angle formed by a contact point of the surfaces 29 and 49, such vertex V being located substantially medial of the closure splay control ramp 35. As a practical matter, the initial point of contact V between the surfaces 29 and 49 (e.g., the acute angle vertex V) should not be located at the closure root surface 27, but rather at or substantially near where the radiused inner corner surface 28 terminates and transitions into the load flank surface 29 as best shown in FIG. 4. With reference to FIG. 5, as the closure 7 is tightened against an insert located within the receiver 10 or directly against a rod connector and the receiver arms 22 experience some outward pivot-splay, a load bearing line or patch of contact may move slightly outwardly away from the radiused surface 28, but remain substantially medial of the closure splay control ramp. FIG. 5 also shows that upon tightening, contact between the splay control ramps 35 and 55 arrests any further pivot-splay of the receiver arms 22. Thus, limited outward pivot-type splay of the receiver arms 22 may occur without unfavorably pre-loading outward portions of the thread 4 of the closure 7 located near the splay control ramp 35. During the rotating and tightening of the closure 7 within the receiver 10, the closure toe 41 remains unloaded and radially outer portions of both load flanks 29 and 49 remain spaced from one another. In the illustrated embodiment translation of the contact line or patch between the load flanks 29 and 49 undergo an outward translation of about one-half the total splay of the receiver arms 22, which typically spread apart about 0.004 to about 0.006 inches. Thereafter, the splay control ramps 35 and 55 mutually engage in a radial direction to interconnect and mechanically lock, resisting any further splaying tendency of the receiver arms 22 for example, in FIG. 3, by the lines Y (along the closure root surface 27) and Z (along the receiver crest 51).

Figure 2:
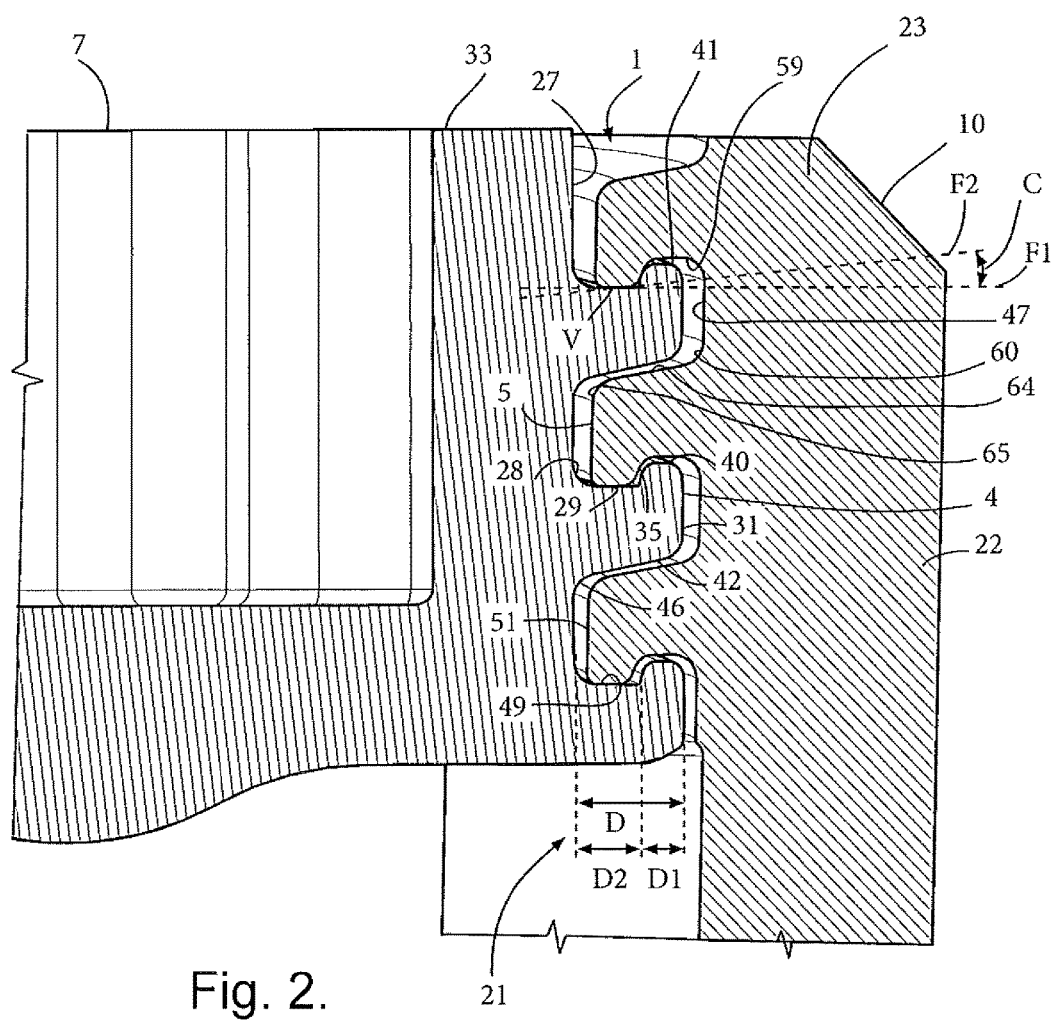
FIG. 2 is an enlarged and partial front elevational view with portions broken away of the closure flange form mechanism of FIG. 1.
Figure 3:
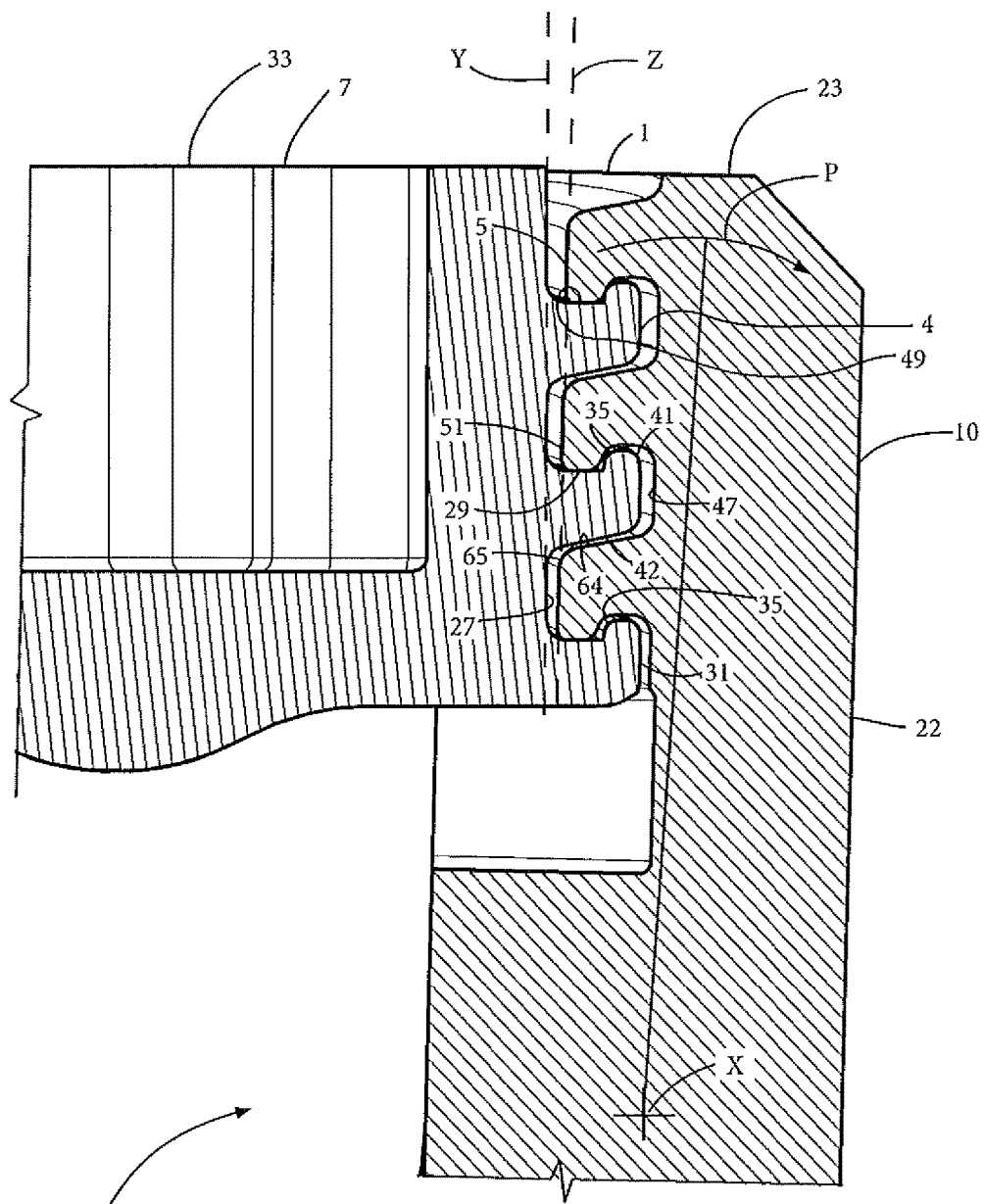
FIG. 3 is another enlarged and partial front elevational view with portions broken away of the closure flange form mechanism of FIG. 1.

As described previously herein, FIGS. 1-6 illustrate the closure 4 and receiver 10 wherein the closure load flank 29 (see extension reference line F1) slopes downwardly and the receiver load flank 49 (see extension reference line F2) is disposed substantially horizontally and such lines intersect at a vertex V at an angle C. With particular reference to FIGS. 2, 4, and 5, it is noted that the angle C decreases slightly, or in some instances, does not substantially change during loading and tightening of the closure 7 within the receiver 10. Rather, a moving contact patch defined in part by the vertex V migrates outwardly a minimal amount, but remains close to the closure root surface 27. The angle C is to accommodate receiver arm pivot (each arm 22) of about one to two degrees, preferably between about 1.2 and about 1.4 degrees for each receiver arm 22 followed by a stop or check of the receiver pivot-splay by engagement of the splay control ramps 35 and 55. Torque applied is generally about 75 to about 90 inch pounds with the illustrated flange forms 4 and 5. Thread pitch can vary, but preferably ranges between about 0.039 inches and about 0.045 inches for smaller flange forms, with larger pitches for larger flange forms.

It is noted that in other embodiments of the invention, as long as an angle C is formed between the load flanks 29 and 49, the flanks need not be in the configuration shown in FIGS. 1-5. For example, the closure load flank 29 could be substantially horizontal and perpendicular to the closure axis A and the receiver load flank 49 could have a reverse angle or undercut. Furthermore, the closure load flank 29 could slope upwardly, requiring a further undercut or greater reverse angle orientation of the receiver load flank 49.

Figure 6:
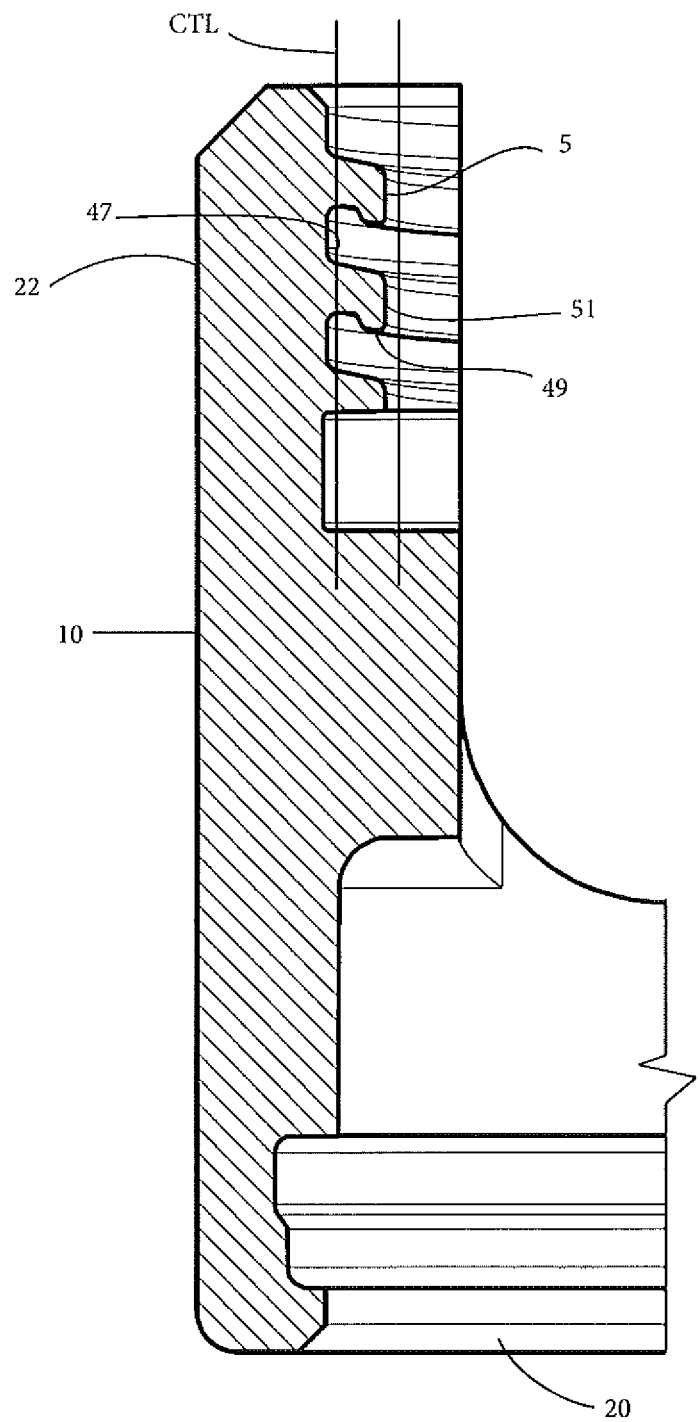
FIG. 6 is an enlarged and partial front elevational view with portions broken away of the receiver of FIG. 1.

With reference to FIG. 6, it is noted that the closure 7 flange form 4 depth D illustrated in FIG. 2 and discussed previously herein is preferably designed by combining both beam (tension) theory and thread theory. It is believed that a larger core diameter ($2R1$) for the closure 7 and a shorter thread depth D thereof is advantageous in decreasing bending moments on the receiver arms 22. This is because such thread loading flanks are positioned closer to a central tension line CTL (see, e.g., FIG. 6 that shows a theoretical central tension line CTL for the receiver 10) within the upwardly extending arms 22 of the U-shaped receiver 10. Moving the root of the male closure flange form 4 outwardly as close as possible to the theoretical tension line CTL in the receiver 10 arms is desirable in that it can decrease a resultant bending moment on the receiver arms 22. By so doing, the outer diameter of the closure top (2R2) measured between crest surfaces 31 can remain the same size for a given receiver 10.

Figure 7:
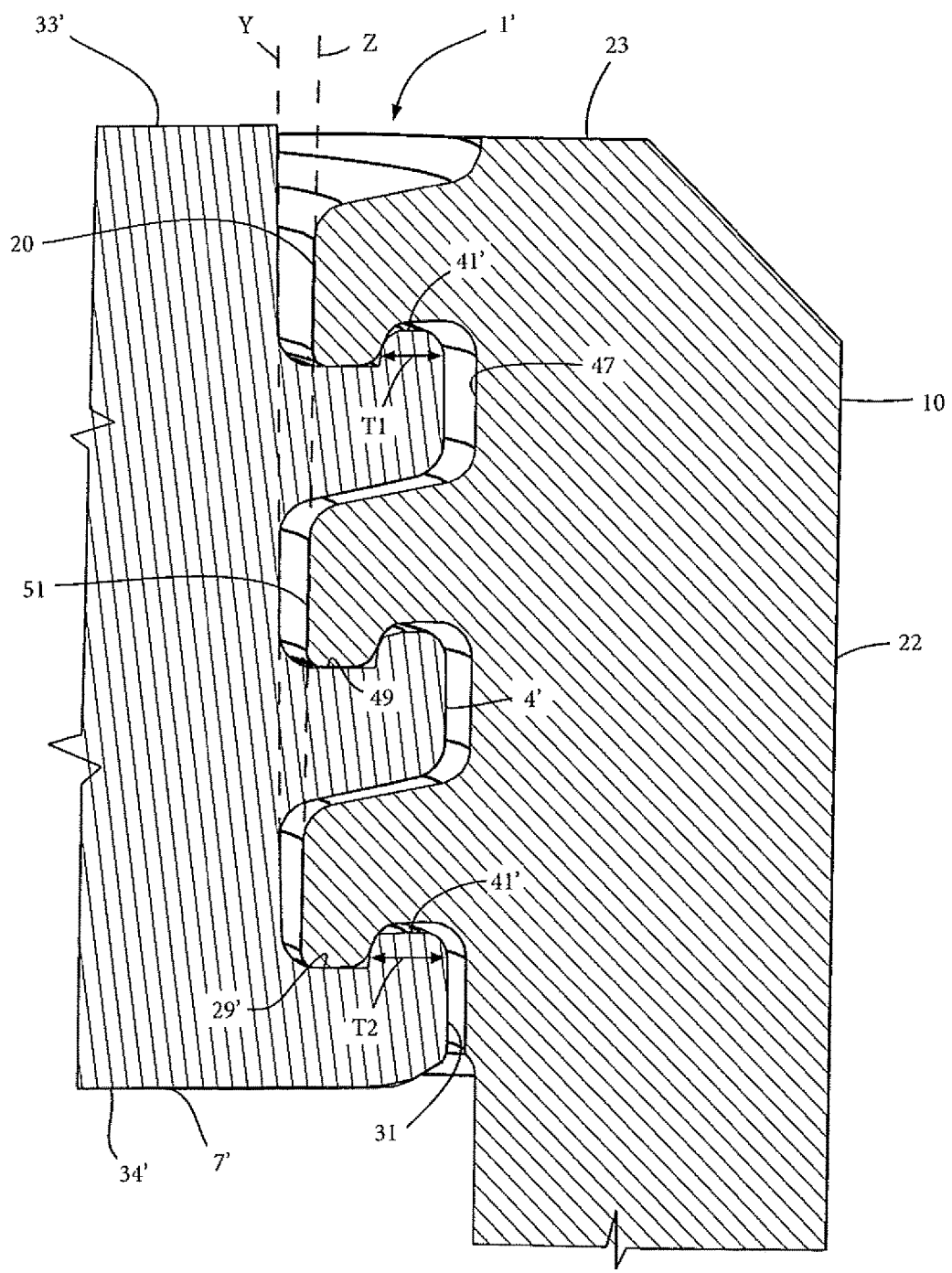
FIG. 7 is an enlarged and partial front elevational view with portions broken away of the receiver of FIG. 1 and shown with an alternative closure, also in partial front elevational view with portions broken away to show the detail thereof.

With reference to FIG. 7, an alternative embodiment of a closure mechanism 1' utilizing an alternative closure 7' with the receiver 10 is shown. The closure 7' is identical to the closure 7 previously described herein with the exception of a radially extending thickness or depth T measured at a toe 41' of the closure flange form 4'. As illustrated in FIG. 7, the thickness T increases gradually from T1 to T2 in a downward spiral direction from a top 33' to a bottom 34' of the closure 7'.

Figure 8:
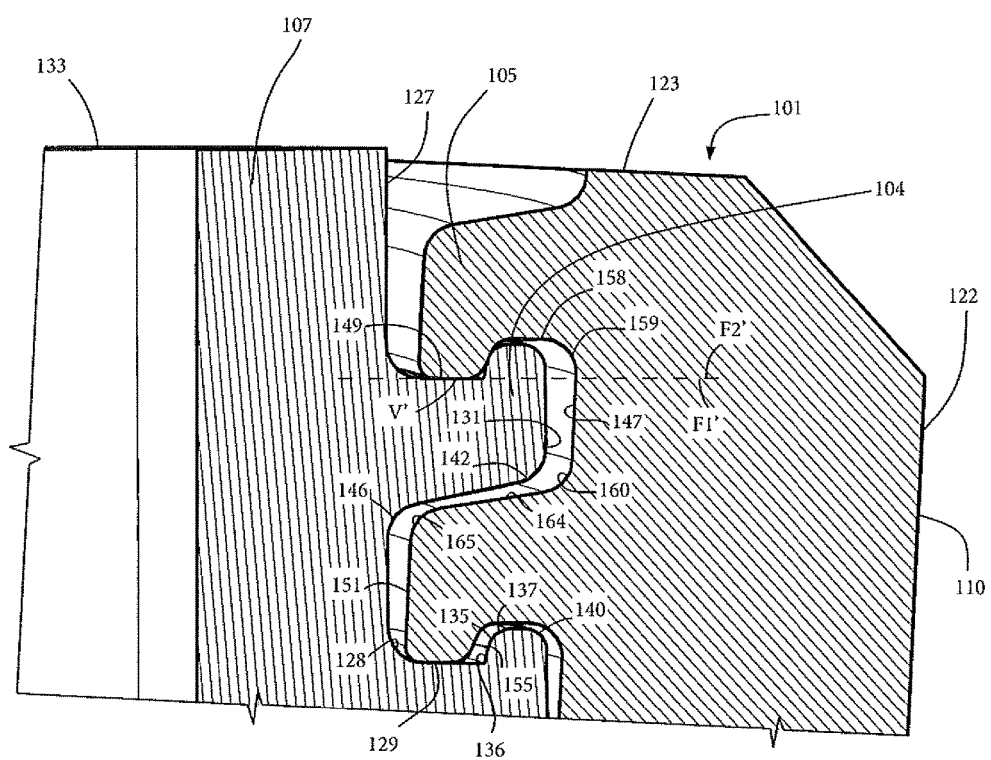
FIG. 8 is a greatly enlarged fragmentary cross sectional view of a first modified embodiment of a spinal implant closure flange form according to the present invention.

With reference to FIG. 8, an alternative embodiment is shown wherein as a closure flangeform 107 is tightened each receiver arm 122 experiences some outward pivot-splay. FIG. 8 shows that upon tightening, contact between the top flange splay control ramps 135 and 155 arrests any further pivot-splay of the receiver arms 122. During the rotating and tightening of the closure 107 within the receiver 110, radially outer portions of both load flanks 129 and 149 engage one another, whereas the other flange toes 141 do not necessarily engage splay control ramps 155. In the illustrated embodiment translation of a contact region or area V' between the load flanks 129 and 149 on the top thread only, after final tightening, and splaying of the receiver arms 122, sequentially in the top flange, both surfaces 129 and 149 would be mating and parallel or flush with one another, such that F1' and F2' are aligned and the angle C' is zero; however, initially the closure loading surface 129 would extend radially in cross section from the closure 107 and the receiver flank surface 149 would initially slope rearwardly in cross section from the crest to the root of the receiver thread 105, preferably the angle rearward being such that the two load surfaces become fully mating and parallel when the closure 107 is fully received in the receiver 110 and fully tightened. It is foreseen that intermediate between the embodiments of FIGS. 7 and 8 could also be utilized.

Figure 9:
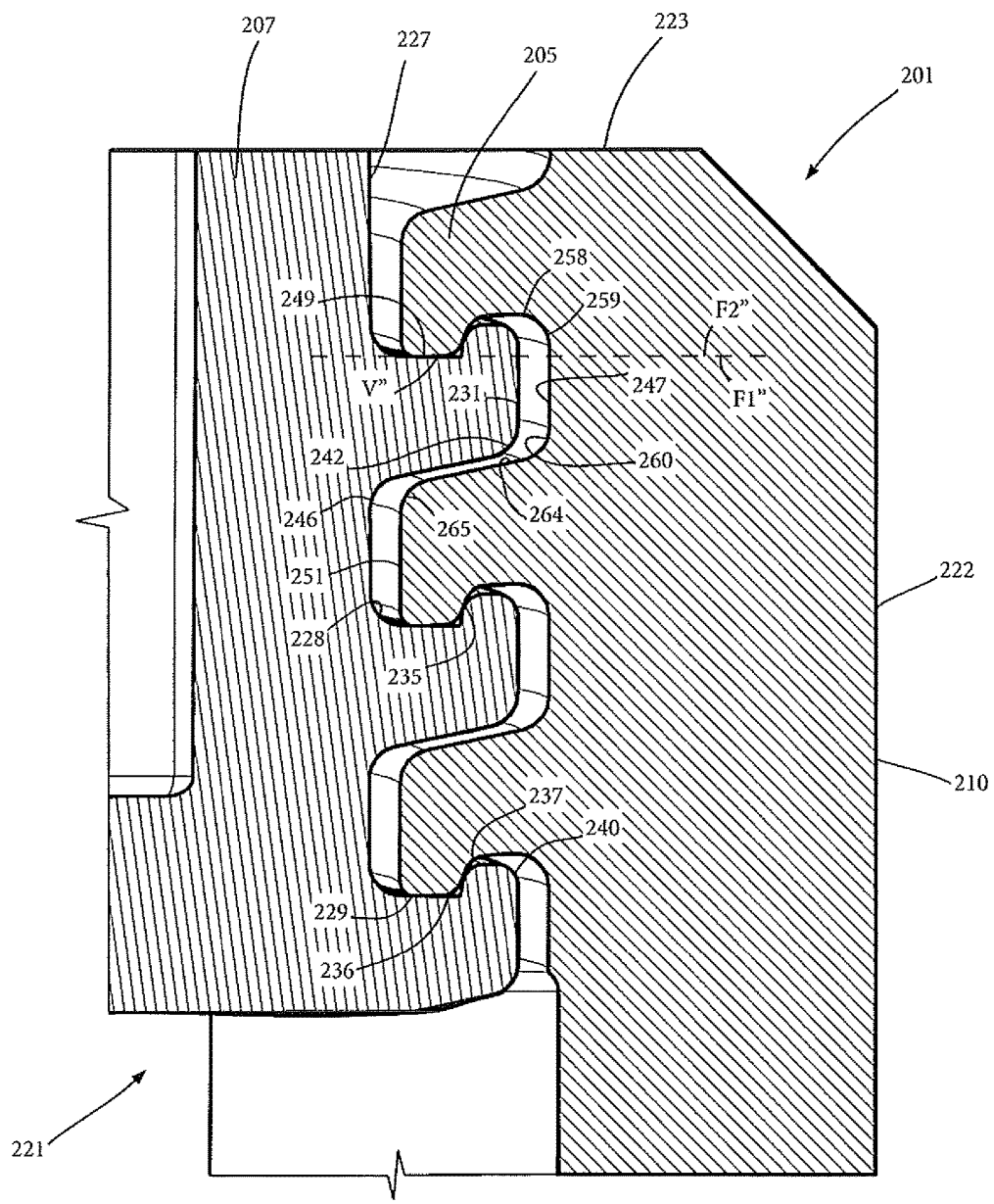
FIG. 9 is a greatly enlarged fragmentary cross sectional view of a second modified embodiment of a spinal implant closure flange form according to the present invention.

With reference to FIG. 9, another alternative embodiment is shown wherein as a closure 207 is tightened each receiver arm 222 experiences some outward pivot-splay. FIG. 9 shows that upon tightening, contact between the splay control ramps 235 and 255 arrests any further pivot-splay of the receiver arms 222 for every tier of the flange form 204 (that is every 360° revolution) sequentially as the flange is tightened and rotated downwardly. During the rotating and tightening of the closure 207 within the receiver 210, radially outer portions of both load flanks 229 and 249 engage one another. In FIG. 9, the contact area or region V''' between the load flanks 229 and 249 on each tier of the flange form 204, after final closure and splaying of the receiver arms 222, mate and are parallel or flush, such that F1" and F2" are aligned and the angle C' is zero; however, initially, each closure loading surface 229 would extend radially in cross section from the closure 207 and each receiver flank surface 249 would initially slope rearwardly in cross section from the crest to the root of the receiver flange 205, preferably the angle rearward is configured so that the two load surfaces become fully mating and parallel in sequence as the closure 207 is fully received in the receiver 210 and fully tightened, as seen in FIG. 7 top flange form. Furthermore, the shape of each tier is slightly different, such that when the closure 207 is fully tightened, the splay control ramps 235 and 255 are in touching relationship or very closely spaced from each other, as compared to the embodiment of FIG. 1, wherein the splay control ramps of only the top tier are in touching or closely spaced relationship to each other and are increasingly spaced with each successive lower tier.

It is to be understood that while certain forms of the present invention have been illustrated and described herein, it is not to be limited to the specific forms or arrangement of parts described and shown.

The invention claimed is:
1. A spinal fixation assembly comprising:
   a closure having a body;
   a closure flange form extending helically about a central axis of the body of the closure;
   a receiver having a first upright arm and a second upright arm;
   a channel formed between the first upright arm and the second upright arm;
   a receiver flange form extending discontinuously along inner surfaces of the first upright arm and the second upright arm of the receiver;
   a closure splay control ramp included in the closure flange form; and
   a receiver splay control ramp included in the receiver flange form and configured to engage the closure splay control ramp, engagement of the closure flange form and the receiver flange form generating a controlled splay during a rotational mating of the closure within the receiver, the controlled splay generating an outward splay of the first upright arm and the second upright arm and reducing torque of the closure during loading of the closure into the receiver, the controlled splay arresting the outward splay of the first upright arm and the second upright arm when the closure is in a locking engagement with the receiver.

2. The spinal fixation assembly of claim 1, wherein the outward splay includes an outward pivot of the first upright arm and the second upright arm.

3. The spinal fixation assembly of claim 1, wherein the receiver flange form includes a receiver load flank and the closure flange form includes a closure load flank.

4. The spinal fixation assembly of claim 3, wherein the receiver load flank is in full contact with the closure load flank upon the locking engagement of the closure with the receiver.

5. The spinal fixation assembly of claim 3, wherein the receiver load flank has an undercut relative to the inner surfaces of the first upright arm and the second upright arm.

6. The spinal fixation assembly of claim 5, wherein the undercut provides an initial contact between the receiver load flank and the closure load flank during the rotational mating of the closure within the receiver.

7. The spinal fixation assembly of claim 3, wherein the receiver load flank is spaced relative to a stab flank.

8. The spinal fixation assembly of claim 3, wherein the closure load flank is spaced relative to a stab flank.

9. The spinal fixation assembly of claim 1, wherein the closure flange form includes a crest surface running relative to a root surface.

10. A spinal fixation assembly comprising:
    a closure having a body;
    a closure flange form extending helically about a central axis of the body of the closure;
    a receiver having a first upright arm and a second upright arm;
    a channel formed between the first upright arm and the second upright arm;

a receiver flange form extending discontinuously along inner surfaces of the first upright arm and the second upright arm of the receiver;

a closure splay control ramp included in the closure flange form; and a receiver splay control ramp included in the receiver flange form and configured to engage the closure splay control ramp, a spacing between the closure splay control ramp and the receiver splay control ramp generating a controlled splay allowance during a rotational mating of the closure within the receiver, the controlled splay allowance generating an outward splay of the first upright arm and the second upright arm, reducing torque, and increasing thrust of the closure during loading of the closure into the receiver, the controlled splay allowance arresting the outward splay of the first upright arm and the second upright arm when a locking thrust is generated within the receiver.

\* \* \* \* \*

UNITED STATES PATENT AND TRADEMARK OFFICE
CERTIFICATE OF CORRECTION

PATENT NO. : 10,206,716 B2
APPLICATION NO. : 15/852866
DATED : February 19, 2019
INVENTOR(S) : Roger P. Jackson et al.

Page 1 of 1

It is certified that error appears in the above-identified patent and that said Letters Patent is hereby corrected as shown below:

In the Specification

In Cross-Reference to Related Applications, Column 1, Line 9, delete "July 21, 2017" and insert --July 31, 2017-- therefor.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*